US012329923B2

(12) United States Patent
Skakoon et al.

(10) Patent No.: US 12,329,923 B2
(45) Date of Patent: Jun. 17, 2025

(54) METERED DOSE TOPICAL APPLICATOR

(71) Applicant: REFLEX MEDICAL CORP., North St. Paul, MN (US)

(72) Inventors: James G. Skakoon, St. Paul, MN (US); Gary W. Thompson, Boise, ID (US)

(73) Assignee: Team Technologies, Inc., Morristown, TN (US)

( * ) Notice: Subject to any disclaimer, the term of this patent is extended or adjusted under 35 U.S.C. 154(b) by 795 days.

(21) Appl. No.: 17/610,139

(22) PCT Filed: May 11, 2020

(86) PCT No.: PCT/US2020/032400
§ 371 (c)(1),
(2) Date: Nov. 9, 2021

(87) PCT Pub. No.: WO2020/227722
PCT Pub. Date: Nov. 12, 2020

(65) Prior Publication Data
US 2022/0218968 A1 Jul. 14, 2022

Related U.S. Application Data

(60) Provisional application No. 62/845,789, filed on May 9, 2019.

(51) Int. Cl.
*A61M 35/00* (2006.01)
(52) U.S. Cl.
CPC .................................. *A61M 35/003* (2013.01)

(58) Field of Classification Search
CPC ........... A61M 35/003; A45D 2200/055; A45D 34/04; B65D 83/0011
See application file for complete search history.

(56) References Cited

U.S. PATENT DOCUMENTS

| 949,163 A | 2/1910 | Stapley |
| 1,499,784 A | 7/1924 | Recker |
| 1,568,178 A | 1/1926 | Noble |
| 2,283,915 A | 5/1942 | Cole |
| 3,353,718 A | 11/1967 | McLay |

(Continued)

FOREIGN PATENT DOCUMENTS

| FR | 2 623 426 A1 | 5/1989 |
| WO | WO 2014/014612 A1 | 8/2014 |

*Primary Examiner* — Donnell A Long
(74) *Attorney, Agent, or Firm* — Luedeka Neely, P.C.

(57) ABSTRACT

A topical applicator of the propel/repel type includes an expandable reservoir with a port, an attachable applicator tip, and a metered dosing system. The reservoir can be a cylindrical housing with a movable elevator movable by a drive mechanism that is initially not engaged to allow filling of a flowable compound through the port, moving the elevator. An actuator, such as a rotating ring or pushbutton may engage the drive mechanism. The drive mechanism can include a one-way ratcheting feature. Metered doses can be dispensed through a hole or holes in the applicator tip by rotating a dosing knob or pushing a pushbutton causing the drive mechanism to advance the elevator. The drive mechanism and the action to dispense metered doses can be combined into a single motion. The drive mechanism can include detent positions that correspond to discrete doses, and can also provide audible and tactile feedback.

18 Claims, 17 Drawing Sheets

(56) References Cited

U.S. PATENT DOCUMENTS

| | | | |
|---|---|---|---|
| 3,616,970 A | | 11/1971 | Baumann et al. |
| 4,139,127 A | | 2/1979 | Gentile |
| 4,810,249 A | | 3/1989 | Haber et al. |
| 4,865,591 A | | 9/1989 | Sams |
| 4,954,000 A | * | 9/1990 | Gueret .................. A45D 40/04 401/172 |
| 5,725,133 A | | 3/1998 | Iaia |
| 5,851,079 A | | 12/1998 | Horstman et al. |
| 6,129,471 A | | 10/2000 | Lang |
| 6,551,611 B2 | | 4/2003 | Elliesen et al. |
| 6,905,272 B2 | * | 6/2005 | Yamanaka ......... B65D 83/0011 401/86 |
| 7,086,564 B1 | | 8/2006 | Corrigan |
| 7,213,994 B2 | | 5/2007 | Phipps et al. |
| 7,303,348 B2 | | 12/2007 | Phipps et al. |
| 8,246,264 B2 | | 8/2012 | Malvar et al. |
| 8,544,684 B2 | | 10/2013 | Perez |
| 8,950,993 B2 | | 2/2015 | Gagne et al. |
| 9,097,571 B2 | | 8/2015 | Phipps et al. |
| 2014/0031323 A1 | | 1/2014 | Perez |
| 2014/0221945 A1 | | 8/2014 | Dos Santos et al. |
| 2016/0129228 A1 | | 5/2016 | Perez |
| 2018/0178968 A1 | | 6/2018 | Phipps et al. |
| 2018/0207413 A1 | | 7/2018 | Skakoon et al. |

\* cited by examiner

METERED DOSE TOPICAL APPLICATOR

CROSS-REFERENCE TO RELATED APPLICATIONS

The present application is a National Phase entry of PCT Application No. PCT/US2020/032400, filed May 11, 2020, which claims priority to U.S. Provisional Application No. 62/845,789, filed May 9, 2019. Said application is incorporated herein by reference.

FIELD OF THE INVENTION

The disclosed invention relates to devices and methods for preparing and dispensing pharmaceutical preparations, such as creams, liquids, and gels that are applied to the skin or other body surface. In particular, the disclosed invention relates to a metered dose topical applicator device suitable for filling with a flowable pharmaceutical compound, and that can be used to accurately dispense that compound and apply it to the body.

BACKGROUND OF THE INVENTION

One modality for administering therapeutic medicaments is by dermal application with subsequent transdermal absorption. This is quite common for hormone therapy, but is also used for pain medications and corticosteroids, among others. The therapeutic agent is typically blended into a carrier cream that is then rubbed onto the skin. Often, the formulation must be individualized for each consumer based on prescribed medicaments and dosages. These formulations are often prepared in compounding pharmacies, who then also prepare a container filled with the formulation and give it to the consumer. These containers are dispensers of various kinds, for example syringes or pump dispensers. Moreover, this modality is not limited to human adults, but can also be suitable for children, babies, and even pets such as cats and dogs.

Dispensing devices called propel/repel containers are common commercially available items used for cosmetics such as lip balm, lipstick, deodorants, antiperspirants, and moisturizers, and also for household and industrial products such as glue and lubricants. These have been adapted for topical application of therapeutic agents.

One of the most common configurations of propel/repel container features a hollow cylinder with a movable floor, female threads formed in the floor, a male-threaded rod passing through the female threads, and a screw knob, integral with the male-threaded rod, captured on one end of the cylinder. The product to be dispensed resides in the cylinder above the elevator. Turning the screw knob one direction forces the elevator upward, propelling the product from the cylinder, with the other direction repelling it. U.S. Pat. No. 1,499,784 to Becker discloses an example propel/repel container of this configuration, in this case for solid or semi-solid products like lipstick.

U.S. Pat. No. 3,616,970 to Baumann adds a closed exit end with an exit hole or holes, making it suitable for liquids and gels. U.S. Pat. No. 4,139,127 adds a ratchet mechanism to prevent repel motion, making it a propel dispenser only. U.S. Pat. No. 1,568,178 to Noble shows a configuration in which the drive screw is disposed entirely outside of the product reservoir, making the reservoir a simple, empty cylinder. U.S. Pat. No. 5,851,079 discloses a one-way ratchet mechanism as well as audible and tactile signals that are tied to metered incremental doses, called clicks, related to the volume of product dispensed.

The prior art also contains dispensers with drive systems that are engageable and disengageable, and that, further, feature the ability to be filled or refilled when the drive is disengaged. An early example is the grease gun shown in U.S. Pat. No. 949,163 to Stapley. This device is, essentially, a screw thread driven syringe with a barrel with an outlet and a moveable plunger. It employs a lever that toggles on and off the engagement of a set of female threads to a threaded screw. Turning the screw expels grease from the outlet of the gun when the drive system is toggled on. When toggled off, the gun may be filled through the outlet because the plunger is not restrained by the thread engagement. Similar devices are disclosed in U.S. Pat. No. 2,283,915 to Cole, U.S. Pat. No. 3,353,718 to McLay, and U.S. Pat. No. 4,810,249 to Haber, et al, all of which could be used for, or are intended for, delivering medicaments.

U.S. Pat. No. 4,865,591 employs an engageable/disengageable drive combined with a metering system that is used to accurately dispense medicament from an attached medicament cartridge. It features a drive plunger with ratchet-style teeth that is engaged by mating toothed blocks to advance a plunger in the cartridge a distance preselected by the metering system. Disengagement of the drive plunger allows it to be quickly reset to a start position when replacing an empty cartridge with a new one.

Topical applicators for pharmaceutical formulations of liquids, creams, and gels with dose metering features also exist in the prior art. Examples of these devices are disclosed in U.S. Pat. Nos. 7,213,994 and 7,303,348 to Phipps, et al, and U.S. Pat. No. 8,544,684 to Perez. These are propel/repel containers of conventional construction with the additions of an indexed dose metering capability, ratchet mechanisms to prevent repel, and audible and tactile dose indicators. These are commercially available as the Topi-CLICK® from DoseLogix and the Ticker™ Transdermal Applicator from BIOSRX, respectively.

Another prior art metered dose topical applicator is disclosed in U.S. Pat. Pub. 2018/0207413 to Skakoon et al, titled "Metered Dose Topical Applicator," which is commercially available as the UnoDose™ metered dose topical applicator from Reflex Medical.

All three of the commercially available applicators mentioned immediately above are best suited for adult patients to apply topical creams to large body surfaces such as a forearm. Even if they dispense small enough volumes per actuation (such as, for example, 50 microliters) their physical size is unsuitable for many applications, an example of which is applying a dispensed cream to the inside of pets' ears.

Thus, "micro-sized" metered dose topical applicators have been developed. Two example devices are the MD™ Pen and MD™ Syringe available from Medisca, Inc. of Montreal, Quebec, Canada. These devices feature an open medicament chamber that is filled with a therapeutic cream by a compounding pharmacy. After filling, a pump assembly with an outlet port is attached to the open end of the chamber. The pump is then actuated by pushing a pushbutton, on the opposite end of the chamber, in a motion similar to a clicking ball point pen. Each push of the pushbutton dispenses a metered dose of the cream out of the outlet port for dermal application. In this case, the dose size is 0.1 or 0.15 milliliters, depending on the model.

Two more examples of micro-sized metered dose topical applicators are the Topical TWIST Pen and the Topical CLICK pen available in the United States through RxCoop of Goldenrod, FL. These devices again feature an open medicament chamber that is filled with a therapeutic cream by a compounding pharmacy. After filling, an applicator tip assembly is attached to the open end of the medicament chamber. Both devices have a screw thread drive system the advances an elevator to expel the cream through a hole or holes in the applicator tip. In the Topical TWIST Pen version, rotating a knob on the opposite end of the medicament chamber advances the elevator. There are also a metering and anti-rotation functions included in the drive mechanism, which also include sensory feedback for the user. In the case of the Topical CLICK pen, pushing a pushbutton on the opposite end of the medicament chamber advances the elevator. This is similar to the action of a clicking ball point pen. Each click dispenses a metered dose and provides sensory feedback to the user. These devices dispense 0.01, 0.025, or 0.05 milliliters per metered dose, depending on the model.

The examples immediately above suffer drawbacks, the most obvious of which is inconvenient and ineffective filling. Because the medicament chambers are long and slender, the cream can only be added by using a long nozzle inserted into the chamber. Even then, filling the chamber without pockets of air is challenging. Moreover, removing any entrapped air bubbles can be almost impossible in some cases. This is especially detrimental to the overall performance and the accuracy of these micro-sized applicators because the metered-dose volumes are so small, and any bubbles can have a large negative effect.

Another example of a micro-sized metered dose applicator is disclosed in U.S. Pat. Application No. 2018/0178968 to Phipps, et al. A device based on this disclosure is commercially available as the Topi-Click MICRO™. This device may be filled with a compounded cream, the volume of which is discretionary between about 1 and 10 milliliters, and dispensed in 50 microliter increments (0.05 milliliters).

Fillable metered dose dispensers of the form disclosed in U.S. Pat. Application No. 2018/0178968 to Phipps, et al include: 1) a free-floating sealing plunger that moves during filling, and 2) a drive system that moves a plunger driver via a user action. The user action that moves the plunger driver first takes up the space, if any, between the plunger and plunger driver then moves the plunger as intended for dose dispensing. This arrangement, however, has disadvantages. In particular, if dispensers of this type are only filled partially, which is often the case, the distance between the plunger driver and the plunger can be large. This means that the dosing means (e.g. a rotating knob) must be actuated numerous times to take up that distance. Motorized tools (i.e. a battery-operated drill) can be employed, but that means having one available. Furthermore, stopping a motorized tool while never overshooting is difficult. Moreover, for the plunger driver to mechanically capture the plunger might be difficult or impossible, meaning that the plunger could possibly move forward during use independent of the plunger driver.

In light of the drawbacks of the prior art, there exists a need for an improved metered dose applicator that can be loaded with a flowable compound to any desired fraction of a full fill, and that can dispense the contents with a minimum of additional user handling steps.

SUMMARY OF THE INVENTION

Embodiments of the disclosed invention feature a device for incrementally metering discrete volumes of a compounded pharmaceutical liquid, cream, or gel formulations, and for topically applying the formulation for dermal absorption. The device is configured to allow any fraction of its maximum fill volume to be loaded when the drive mechanism is not engaged, yet allow the drive to be fully engaged immediately when desired by triggering an actuating element.

Embodiments can also include additional advantageous features as described in the following: Embodiments can include a connection port through which compounded formulations may be introduced into an expandable and collapsible storage reservoir.

Embodiments can include a means of collapsing a storage reservoir, thus propelling the formulations out of the storage reservoir.

Embodiments can include an accurate means of propelling the formulation out of the device through the tip, such as an elevator driven by a drive mechanism comprising a screw thread and drive nut, which, in turn, may be actuated by user action such as rotating a knob.

Embodiments can include an actuating means that engages a drive mechanism upon demand.

Embodiments can include an attachable tip for the device with a plurality of openings to allow outflow of the formulation, and to provide a means of hands-free topical application of the formulation.

In embodiments, the nut can have flexible fingers with threaded portions at one end, a tubular end portion with cooperating ratchet portion at an opposing end. The cooperating ratchet portion may comprise a plurality of detent portions that engage recesses or openings in a surface of the container housing. In embodiments, the recesses or openings may be positioned on a plate unitary with a barrel portion or sub-assembly of the container housing and may provide audible and/or tactile indication of incremental rotations corresponding to indexed metered doses.

In embodiments, the nut can have flexible fingers with threaded portions that are initially not engaged with screw threads of a drive mechanism, but that can be flexed via an operator actuation to become engaged.

Embodiments can include an indexing means that partitions the propelled formulation into metered doses.

Embodiments can include audible and tactile indications corresponding to the indexed metered doses.

Embodiments can include a one-way, or ratcheting, mechanism to prevent reversing of the propel action (repel).

Embodiments can include other useful features such as volumetric or other measurement scales, protective covers, and ergonomic geometric elements.

A further feature and advantage of the invention is that of a container housing configured as a barrel and elevator defining a reservoir that is conducive of holding a wide range of volumes of a compounded pharmaceutical liquid, cream, or gel formulation without needing a time consuming rotation of a knob to move the elevator forward, thereby bringing the liquid, cream, or gel formulation to the dispensing tip.

DETAILED DESCRIPTION OF THE INVENTION

Figure 1:
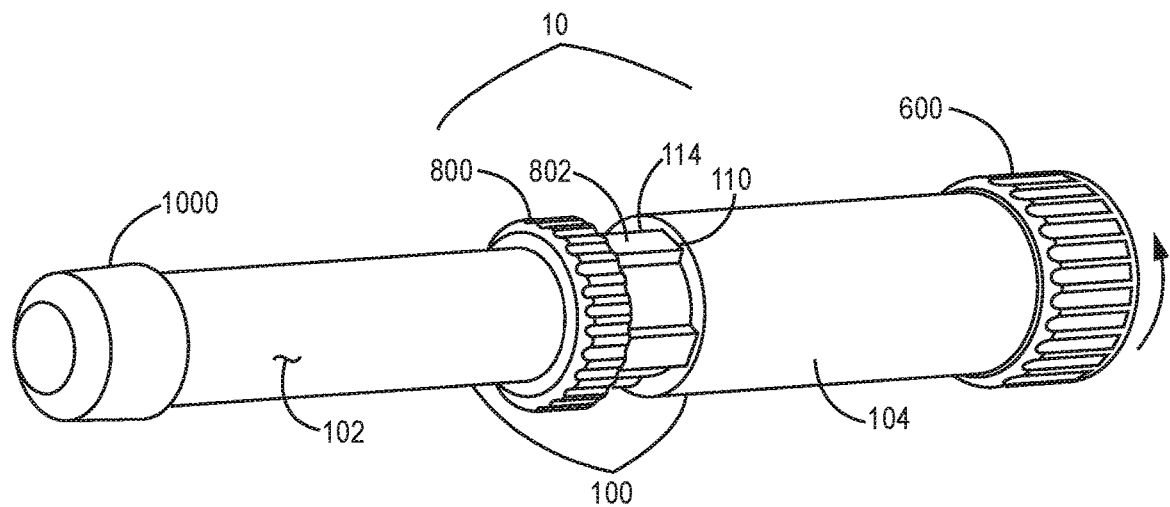
FIG. 1 is a perspective view of an embodiment of the metered dose topical applicator.

Referring to FIG. 1, an embodiment of a metered dose topical applicator 10 in accordance with the present invention is shown. The applicator 10 includes a barrel 100, which has two regions, a medicament reservoir 102 and a mechanism housing 104. The applicator 10 also includes a cover 1000, a drive actuator 800, and a dosing knob 600, the functions of which are explained in detail below.

Figure 2:
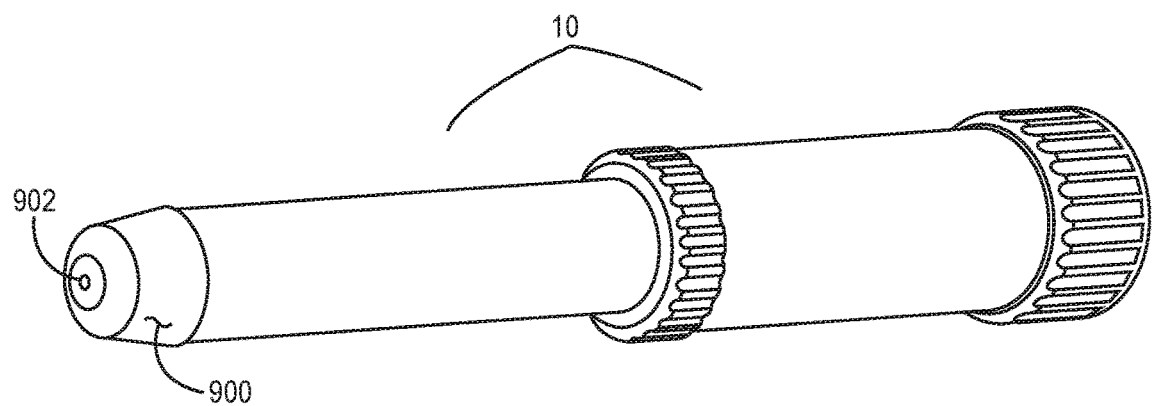
FIG. 2 is another perspective view of an embodiment of the metered dose topical applicator of FIG. 1 showing another configuration.

FIG. 2 shows the applicator 10 with cover 1000 removed to show an applicator tip 900, which is used to topically apply cream that has been metered from the applicator 10.

The applicator tip 900 has an exit hole 902 through which the cream is dispensed from the applicator 10.

Figure 3:
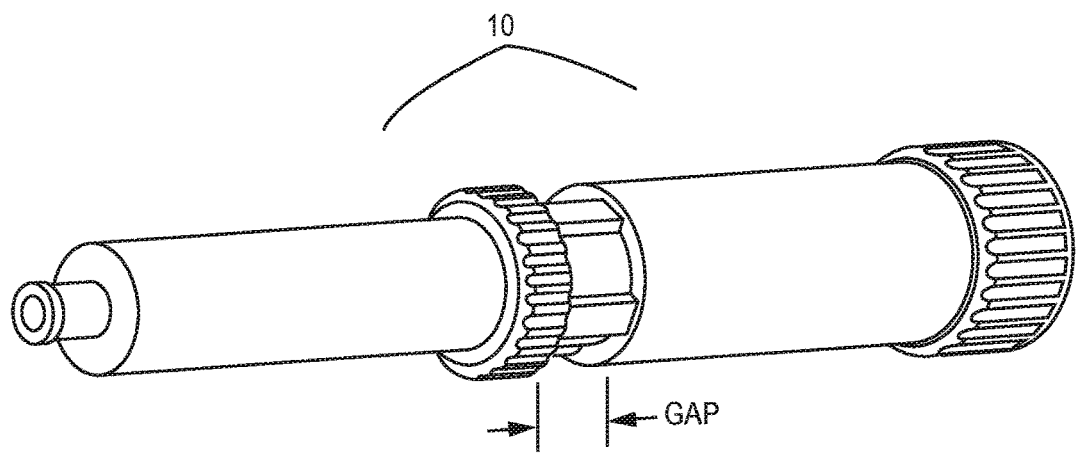
FIG. 3 is another perspective view of an embodiment of the metered dose topical applicator of FIG. 1 and FIG. 2 showing another configuration.

FIG. 3 shows the applicator 10 in a configuration suitable for filling with a compounded cream. The applicator tip 900 has not yet been assembled, and the drive actuator has not been actuated, as shown by the notated gap shown in FIG. 3. This configuration represents how applicator 10 may be provided to the user for preparation.

Figure 4:
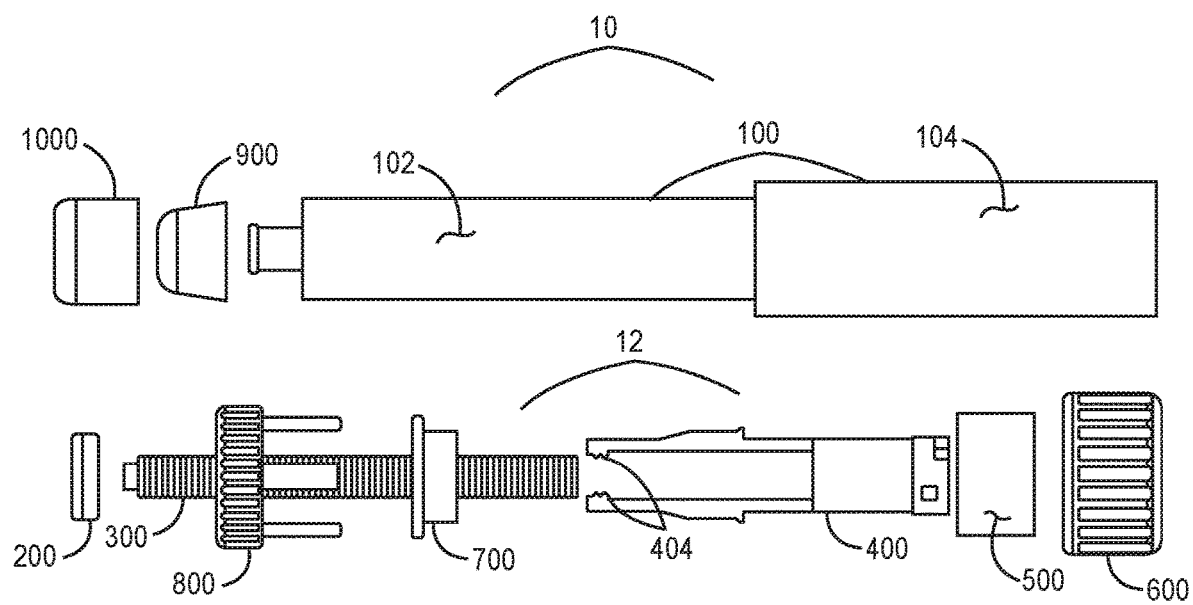
FIG. 4 is an exploded orthogonal view showing the components of the applicator individually.

Referring now to FIG. 4, internal components of one embodiment of applicator 10 are shown in an exploded view. Barrel 100 (with housing 104 and medicament reservoir 102), applicator tip 900, and cover 1000 have been exploded sideways for clarity, although in the actual assembly are coaxial with the other components. An elevator 200 sealingly and slidably rides in barrel 100 defining a volume in medicament reservoir 102. Elevator 200 attaches to drive screw 300. Drive nut 400 includes nut threads 404, which are configured initially as disengaged to drive screw 300, yet are engageable upon demand. Dosing knob 600 attaches to drive nut 400 via, for example, snap fit features. Retainer 500 assembles into housing 104 and provides capturing features that retain and position the rotatable subassembly of dosing knob 600 and drive nut 400. An important function included in applicator 10 is its drive mechanism 12, which comprises dosing knob 600 connected to drive nut 400, which threadably and electively couples to drive screw 300 by way of the action of locking ring 700. Briefly, rotating dosing knob 600 (as shown on FIG. 1) turns drive nut 400, which axially advances drive screw 300. Drive screw 300 likewise pushes on elevator 200, meaning that drive mechanism 12 expels cream out of applicator tip 900 of applicator 10.

Figure 5:
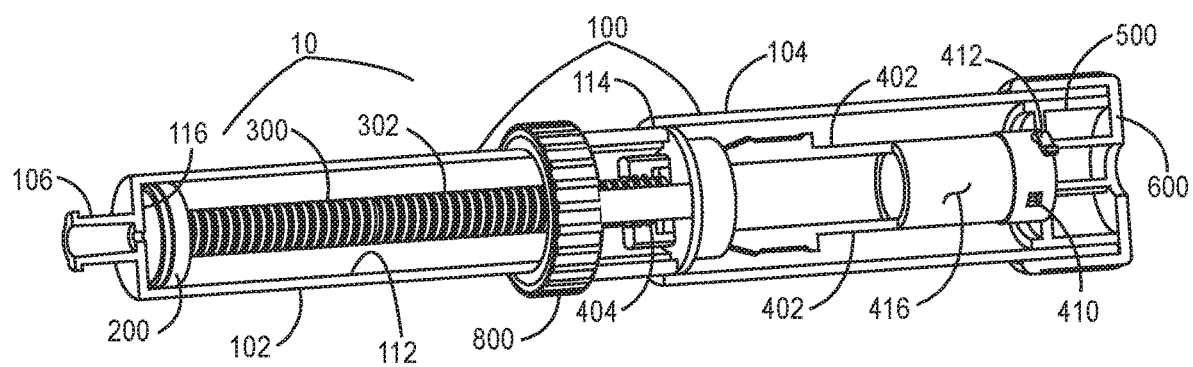
FIG. 5 is a perspective, partially cut-away view showing the applicator in one configuration.
Figure 6:
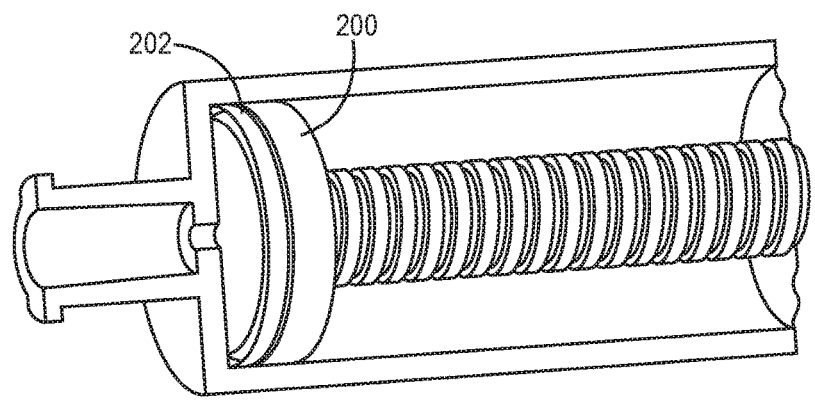
FIG. 6 is a detailed perspective view of one end of the applicator.

Referring now to FIG. 5, elevator 200 is shown in the empty position within medicament reservoir 102 of barrel 100, meaning that the compounded cream capacity of applicator 10 is substantially zero. As shown in FIG. 6, elevator 200 includes a seal lip 202 that sealingly and slidably engages with the internal wall 112 of medicament reservoir 102. In this embodiment, elevator 200 is separate from, but attaches to drive screw 300, for example by a press or snap fit. Nevertheless, elevator 200 and drive screw 300 can be a single component without affecting the essence of the disclosed invention. Moreover, elevator 200 can be made from an elastomer, or can include an elastomer seal such as an O-ring, or can include a plurality of sealing lips, any of which could improve the seal integrity as required.

Figure 7:
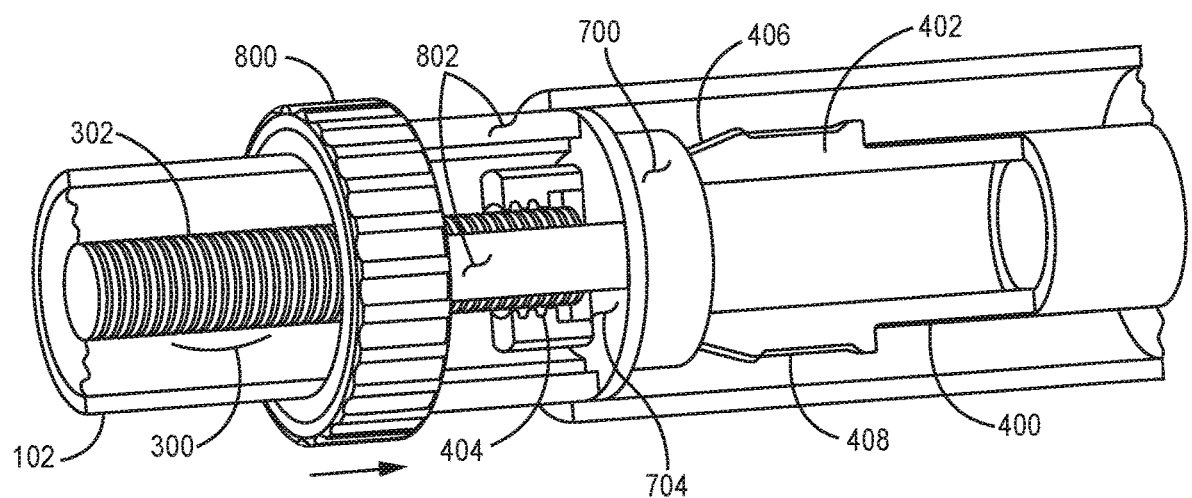
FIG. 7 is detailed perspective view, partially cut away, showing a middle portion of the applicator.

Referring to FIG. 5 and detail FIG. 7, drive screw 300 includes screw threads 302, which can engage with nut threads 404 of drive nut 400, which arrangement is shown here. Nut threads 404 are not yet engaged with screw threads 302 in FIG. 7, but become engaged during use of applicator 10, as is further explained below.

Figure 8:
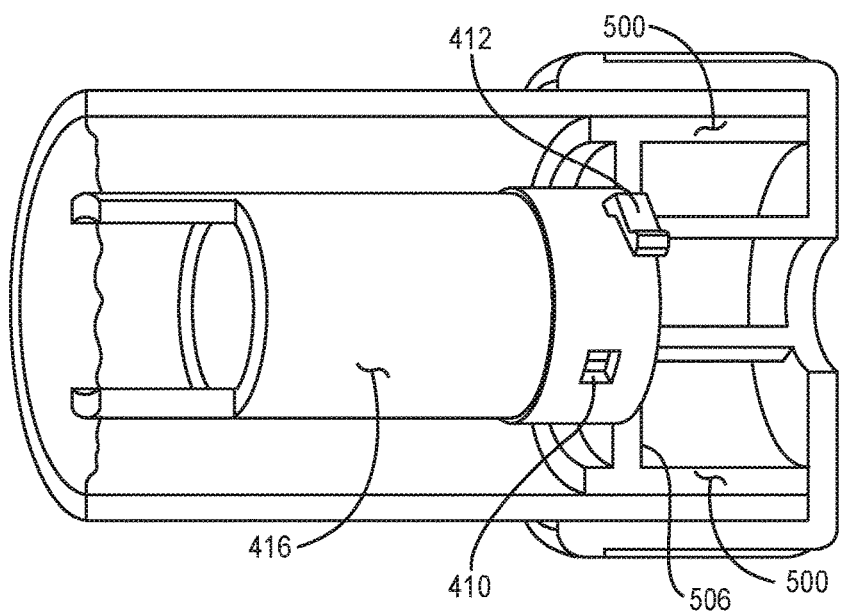
FIG. 8 is detailed perspective view, partially cut away, showing the other end of the applicator.

Referring back to FIG. 5, nut threads 404 are integral with nut leg(s) 402, which extends back to nut body 416. Nut body 416 includes pawl(s) 412 and snapfit slot(s) 410, which are also shown in detail FIG. 8. Retainer 500 is shown in its assembled position within housing 104 of barrel 100. Retainer 500 may be affixed to housing 104 in various ways including a press or snap fit, adhesives, or welding. Retainer 500 includes retainer flange 506.

Figure 9:
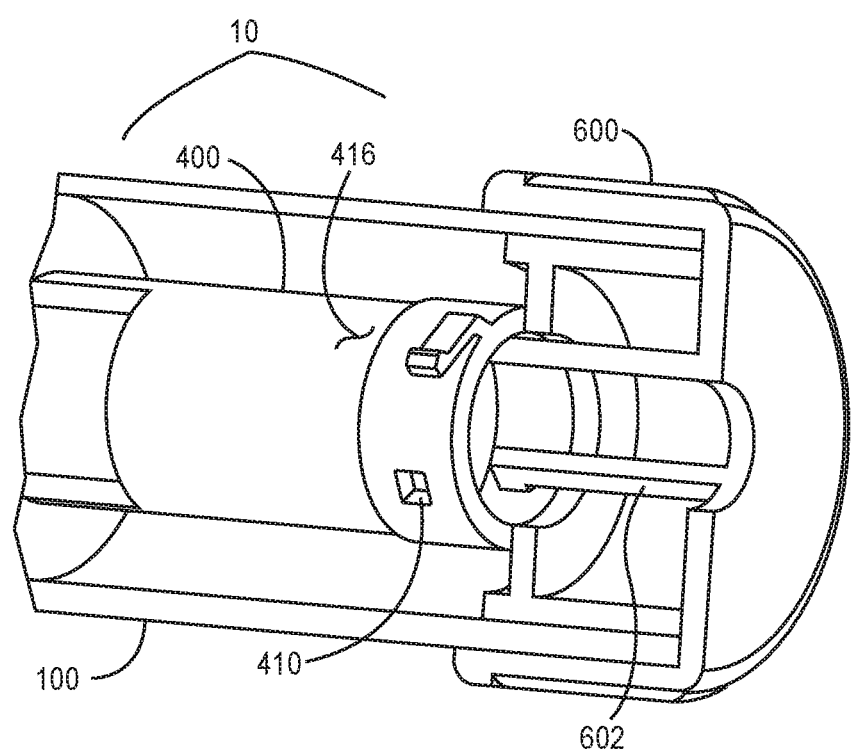
FIG. 9 detailed perspective view, partially cut away, showing the same end of the applicator as shown in FIG. 8, but viewed from a different angle.

Referring now to FIG. 9, dosing knob 600 is shown in its assembled position, in which snapfit leg(s) 602 have snapped into snapfit slot(s) 410 of nut body 416 in a typical snap-fit arrangement. Dosing knob 600 may be connected to drive nut 400 in various ways, the only functional criteria being that once the connection is made between drive nut 400 and dosing knob 600, those two parts, once affixed together, are accurately and stably positioned within barrel 100, yet are free to rotate about the main axis of applicator 10.

Figure 10:
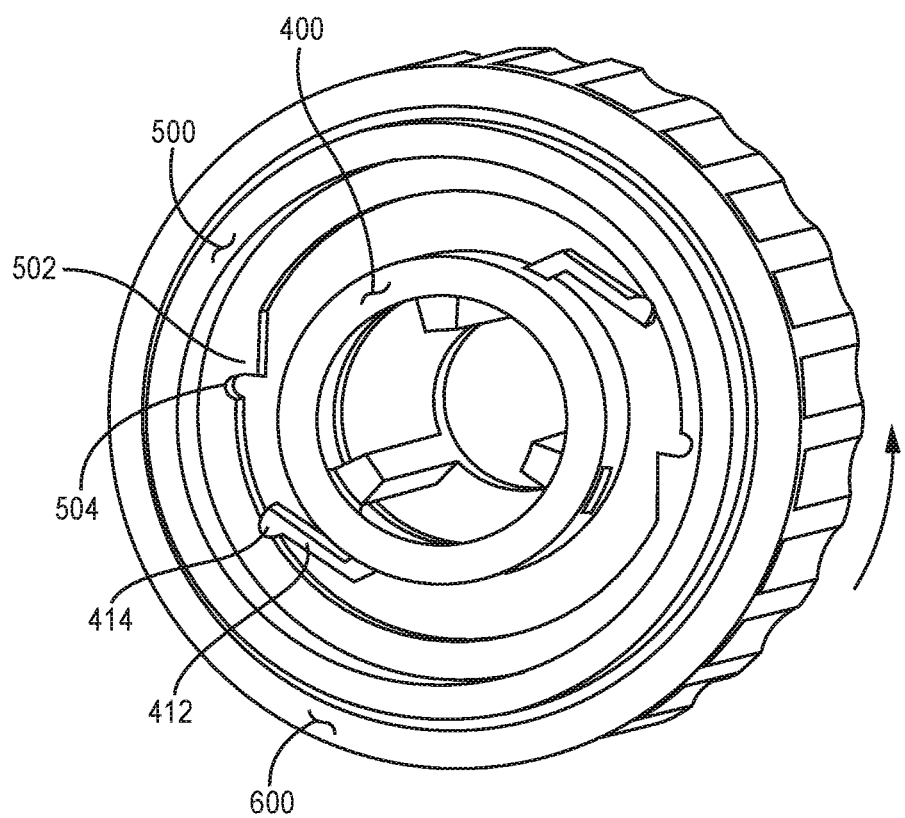
FIG. 10 is a detailed perspective cross-section view showing components of the end of the applicator shown in FIG. 8 and FIG. 9.

Referring now to FIG. 10, retainer 500 includes ratchet tooth 502 and detent nest 504, both of which work together with pawl 412 and detent bump 414, which is integral with pawl 412. Ratchet tooth 502 and pawl 412 allow rotation of drive nut 400 (and dosing knob 600) in one direction, as shown by the arrow, yet check rotation in the opposite direction. Moreover, pawl 412 and ratchet tooth 502 can create an audible indicator of the passing of pawl 412 past ratchet tooth 502, as is typical for ratchet and pawl mechanisms. Detent bump 414 and detent nest 504 work together to provide a stable detent position or positions at various rotational locations. This keeps the dosing knob 600 (and drive nut 400) from rotating inadvertently while applicator 10 is not actively being used.

Referring back now to FIG. 5 and detail FIG. 7, nut leg 402 includes lock ramp 406 and lock nest 408, whose purpose is to work together with locking ring 700 to effect engagement of nut threads 404 with screw threads 302, as explained below. Drive actuator 800 is concentrically retained on the outer diameter of medicament reservoir 102, yet is axially slidable between predefined stop positions. Drive actuator 800 includes actuator leg(s) 802 that contact locking ring face 704. Thus pushing drive actuator 800 (to the right as shown in FIG. 7), will simultaneously push locking ring 700 to the right. Referring momentarily back to FIG. 1, barrel 100 includes a step feature, barrel stop 114, between medicament reservoir 102 and housing 104, which includes barrel slots 110 of barrel 100 through which actuator leg(s) 802 of drive actuator 800 fit. This combination acts to align and retain drive actuator 800 in its position.

Referring back to FIG. 7, as drive actuator 800 pushes locking ring 700 to the right, lock ramp 406 of nut leg 402 works together with guide slot 702 (see FIG. 12) of locking ring 700 to deform nut leg(s) 402 inward, which deformation engages nut threads 404 with screw threads 302. Once locking ring 700 reaches its final position, it will be captured in lock nest 408 of nut leg 402, and will rotate together with nut when dosing knob 600 (FIG. 5) is rotated.

Figure 11:
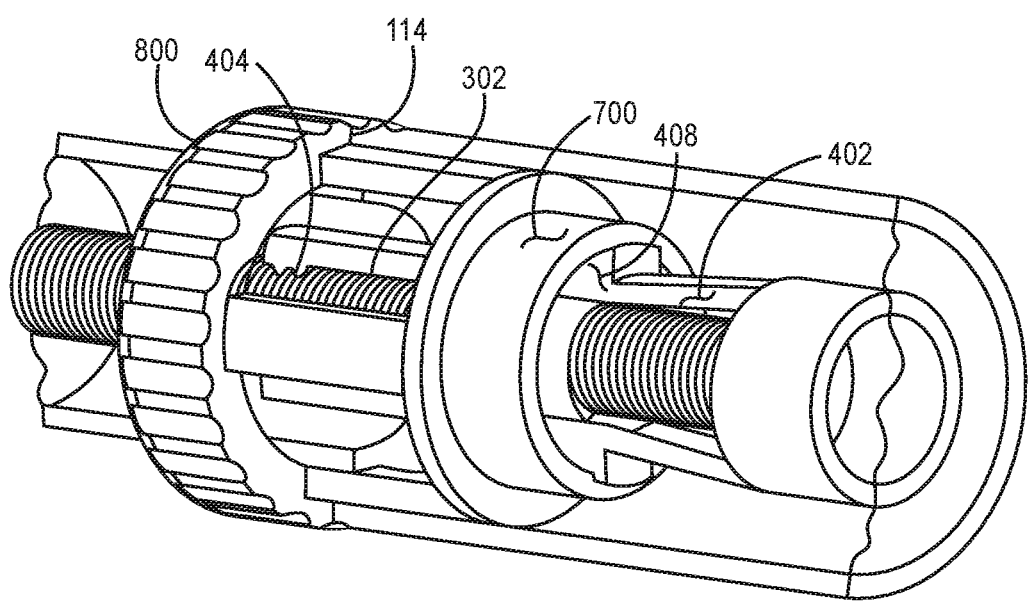
FIG. 11 is a detailed perspective view, partially cut away, showing a middle portion of the applicator similar to FIG. 7, but in another configuration and from a different direction.

Referring now to FIG. 11, drive actuator 800 has been pushed inward, or to the right, until it contacts barrel stop 114, which action has also pushed locking ring 700 in the same direction, which has engaged nut threads 404 with screw threads 302, and which has positioned locking ring 700 into a secure position in lock nest 408. Nut leg 402 is essentially a cantilever spring, and has been deformed inward by locking ring 700.

Figure 12:
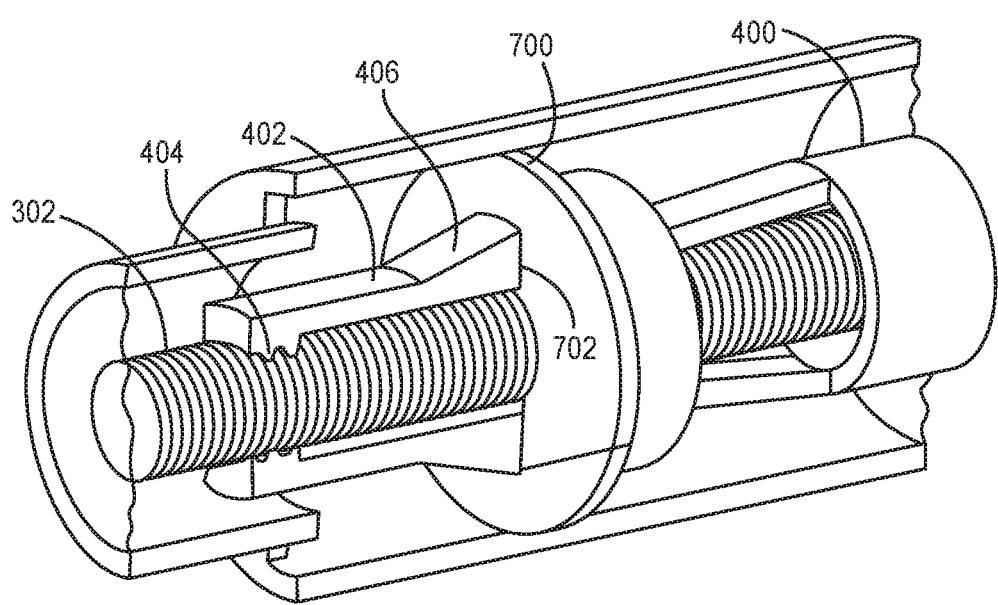
FIG. 12 is detailed perspective view, partially cut away, showing a middle portion of the applicator similar to FIG. 7, but in another configuration and with a component or components hidden.

Referring to FIG. 12, locking ring 700 is shown in the locked position to where it has moved past lock ramp 406 into lock nest 408 (see FIG. 7). (Drive actuator 800 has been hidden in FIG. 12 for a clearer view.) Guide slot 702 of locking ring 700 aligns and guides locking ring 700 along nut leg 402. Because of the inward deflection of nut leg 402, nut threads 404 are engaged with screw threads 302, as shown. As previously noted, locking ring 700 rotates with drive nut 400 and dosing knob 600 (not shown in FIG. 12).

Figure 13:
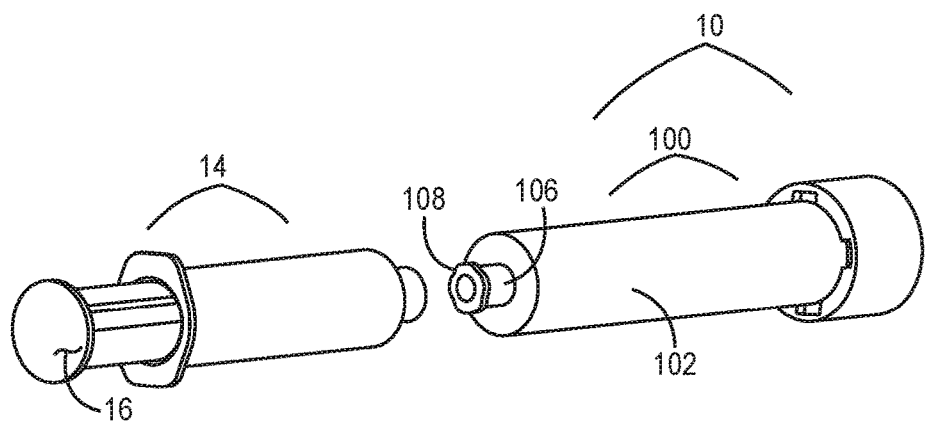
FIG. 13 is a perspective view of one end of the applicator and with a filling syringe aligned to be attached to the applicator.

FIG. 13 shows access port 106 of barrel 100. Access port 106 includes port connector 108, which can be, for example, a Luer style connector, in this case a male Luer lock. Any suitable connector style may be used, but a Luer configuration allows port connector 108 to attach directly to a Luer-tipped syringe (syringe 14 as shown). Syringe 14, when connected, allows drug carriers such as liquids, creams, or gels to be added to medicament reservoir 102 of applicator 10 by pushing syringe plunger 16 forward.

We now turn to an explanation of the physical functionality of the present invention during use by referring to FIG. 5. Applicator 10 may be supplied to a pharmacy for preparation in an empty state with elevator 200 substantially seated against end face 116 of barrel 100. Thus, the volume held by medicament reservoir 102, which is defined by the inside diameter of medicament reservoir 102 and the distance between end face 116 and elevator 200, is substantially zero. Because nut threads 404 are not engaged with screw threads 302, elevator 200 (and drive screw 300) are free to move along the central axis of applicator 10. Thus, for example, if syringe 14 has been used to inject a cream through access port 106 as shown in FIG. 13, elevator 200 (and drive screw 300) will move to accommodate a carrier cream 22 (not shown) by increasing the volume of medicament reservoir 102.

Once the desired volume of a medicament and carrier cream 22 has been added to applicator 10, drive actuator 800 is pushed in until it butts against barrel stop 114, which, as explained above, engages nut threads 404 with screw threads 302, which means the drive mechanism 12 (see FIG. 4) of applicator 10 is likewise engaged.

Because the drive mechanism 12 is not engaged, i.e. nut threads 404 not meshed with screw threads 302, during filling of applicator 10, any desired percentage of fill volume, from 0 to 100% of medicament reservoir 102, may be introduced. Engaging the drive mechanism 12 after filling, regardless of the fill volume, means the drive mechanism 12 is engaged only when desired, but immediately engaged when desired, with the single action of pushing drive actuator 800 to the position shown in FIG. 2. Thus there is no need for a priming or take-up operation to accommodate medicament reservoir 102 fill volumes of less than 100%.

Figure 14:
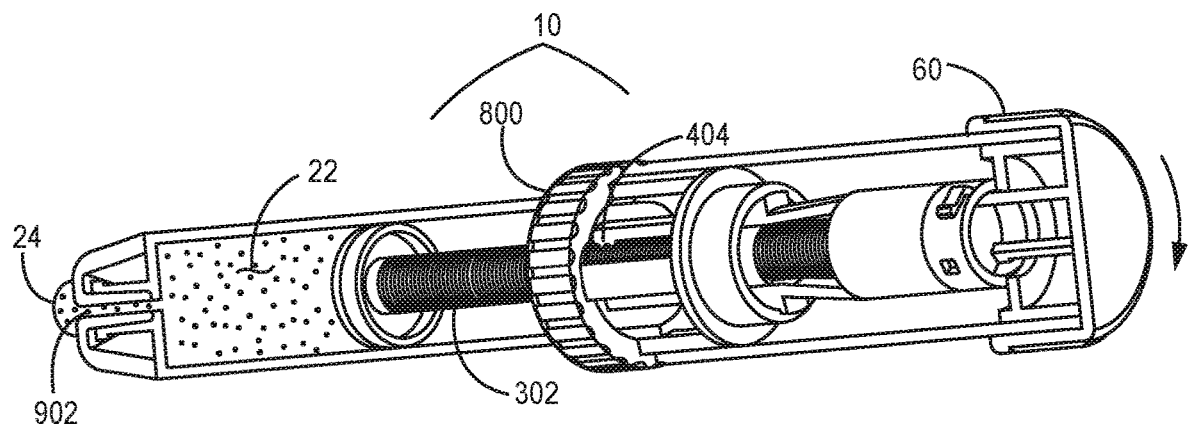
FIG. 14 is a perspective, partial cut-away view of a partially filled applicator that has dispensed a dose.

Actual dosing is shown in FIG. 14 wherein applicator 10 contains a quantity of carrier cream 22, which can hold a suitable medicament. Drive actuator 800 has been pushed in, engaging nut threads 404 with screw threads 302 as described above. Doing knob 600 has been turned in the direction shown so that a dose 24 of carrier cream 22 has been expelled out exit hole 902 of applicator tip 900, and dose 24 is ready of application to the intended site.

Figure 15:
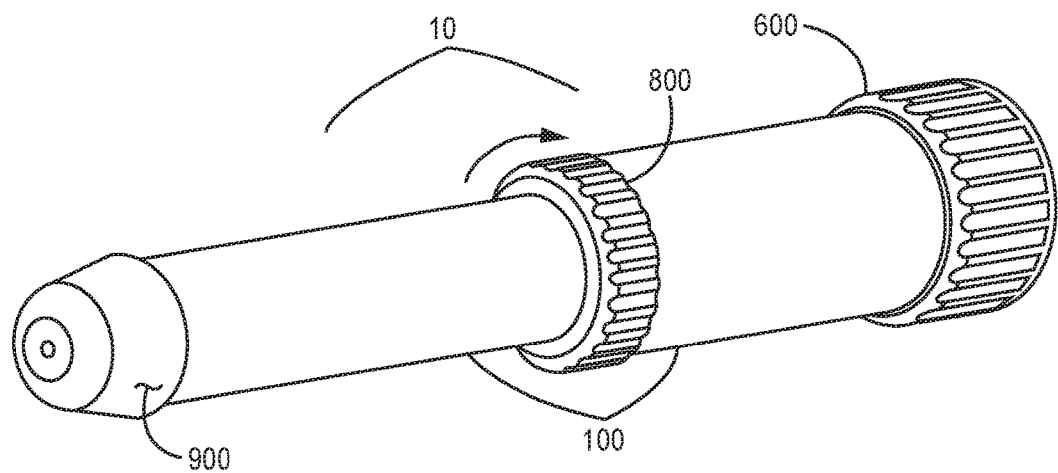
FIG. 15 is a perspective view of the applicator after filling.

Numerous other construction arrangements are possible that embody the functional characteristics of the present invention. For example, in FIG. 15, a metered dose topical applicator 10 is shown in which its drive mechanism is also not engaged during filling, as described above. Applicator 10 also includes barrel 100, dosing knob 600 and applicator tip 900. In this alternative embodiment, however, the drive mechanism is engaged by rotating drive actuator 800 as shown, which engages nut threads and screw threads, which have been arranged internally to engage by this alternate action.

Figure 16A:
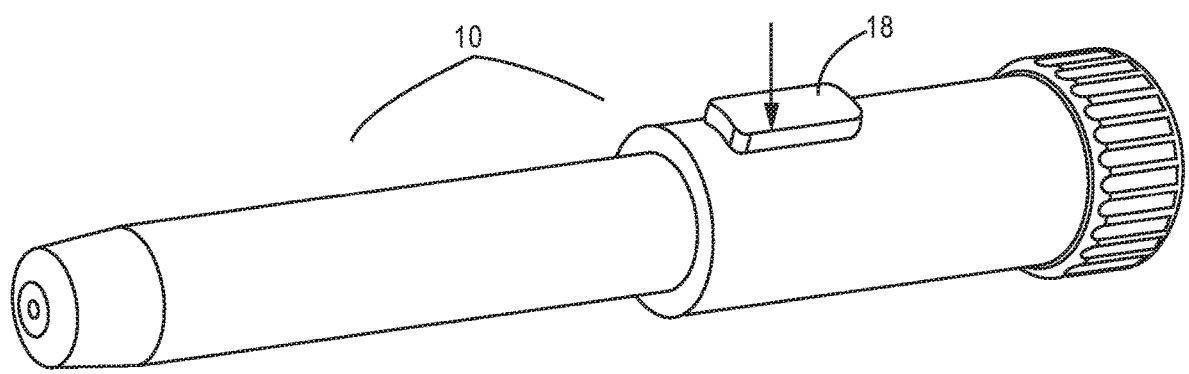
FIGS. 16A and 16B are perspective views showing an alternate embodiment of a metered dose applicator.
Figure 16B:
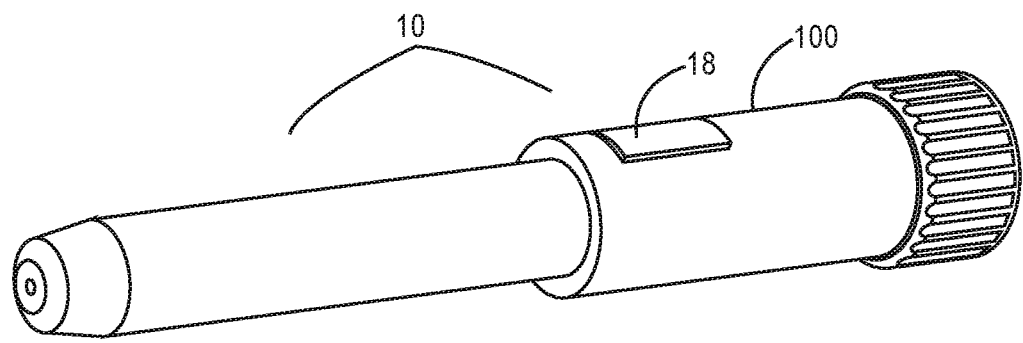

Likewise, FIG. 16A shows an embodiment wherein metered dose topical applicator 10 includes side pushbutton 18. After filling, side pushbutton 18 is pushed as shown by the arrow, which engages the drive mechanism in a fashion similar to what is described above. Side pushbutton 18 can latch, for example, in the pushed position to present a smooth outer surface to barrel 100 as shown in FIG. 16B.

Figure 17A:
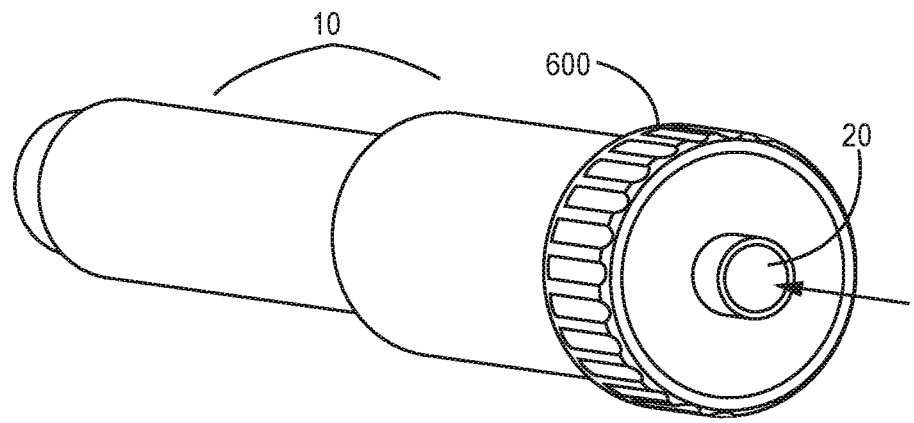
FIGS. 17A and 17B are perspective views showing another alternate embodiment of a metered dose applicator.
Figure 17B:
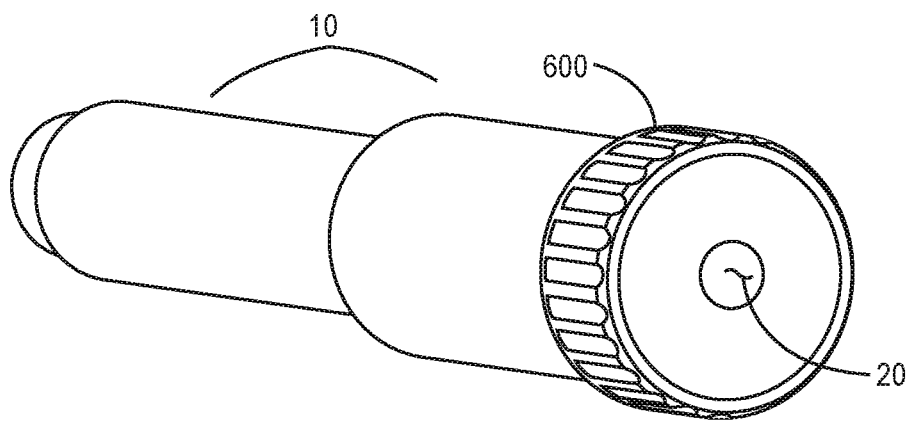

An alternative embodiment is shown in FIG. 17A, wherein applicator 10 has a drive mechanism that, as before, is not engaged to accommodate filling. Applicator 10 includes end pushbutton 20 that can be positioned proud of dosing knob 600 during filling, but when pushed as shown can trigger engagement of nut threads with screw threads as before. End pushbutton 20 can latch in a position flush with dosing knob 600 to present a smooth appearance, and to visually indicate engagement status as shown in FIG. 17B.

Figure 18:
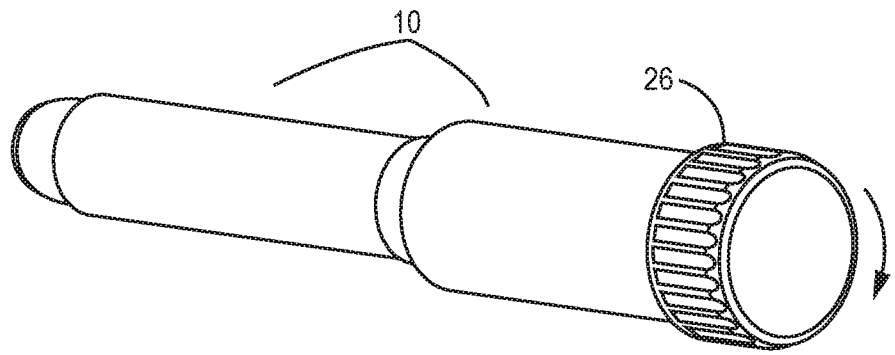
FIG. 18 is a perspective view showing another alternate embodiment of a metered dose applicator.

Another alternative embodiment is shown in FIG. 18. In this embodiment, the drive system is also initially not engaged to accommodate filling. Applicator 10 includes a dosing knob 26, much like before, but in this embodiment, dosing knob 26 serves the dual function of also being the drive actuator. Thus, after the applicator has been filled with cream, dosing knob 26 is rotated as shown. This first causes the drive system's nut threads to engage with the screw threads, analogous to the internal action previously disclosed. Thereafter, rotating dosing knob 26 meters doses with sensory feedback and anti-rotation features as with other embodiments.

Figure 19A:
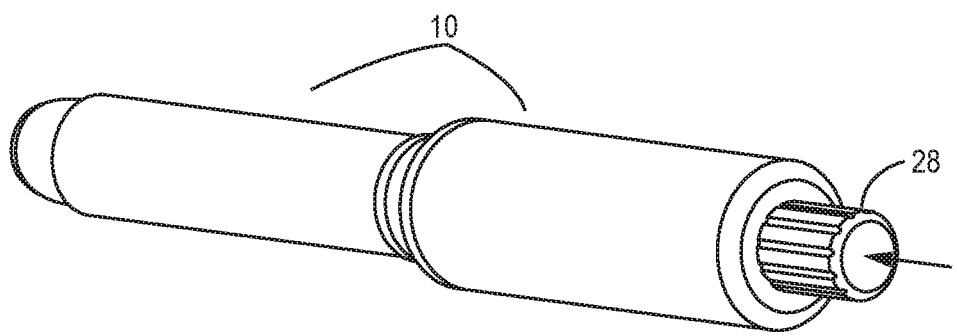
FIGS. 19A and 19B are perspective views showing an alternate embodiment of a metered dose applicator.

Another alternative embodiment is shown in FIG. 19A. In this embodiment, the drive system is also initially not engaged to accommodate filling. In this embodiment, however, rather than a rotating knob, a pushbutton 28 is used to activate the metered doses. Moreover, pushbutton 28 can serve the dual function of also being the drive actuator. Thus, after the applicator has been filled with cream, pushing pushbutton 28 first causes the drive system's nut threads to engage with the screw threads, analogous to the internal action previously disclosed. That could, for example, put pushbutton 28 in the location shown in FIG. 19B. Pushing further on pushbutton 28, until it stops, then meters a dose by way of an internal drive mechanism similar to previously disclosed embodiments. In other words, pushing pushbutton 28 can rotate a drive nut, which then translates a screw, advances an elevator, and expels cream from the medicament reservoir. Releasing pushbutton 28 allows it to return to the position shown in FIG. 19B by way of a return spring for example, which readies the applicator for another dose activation.

Figure 19B:
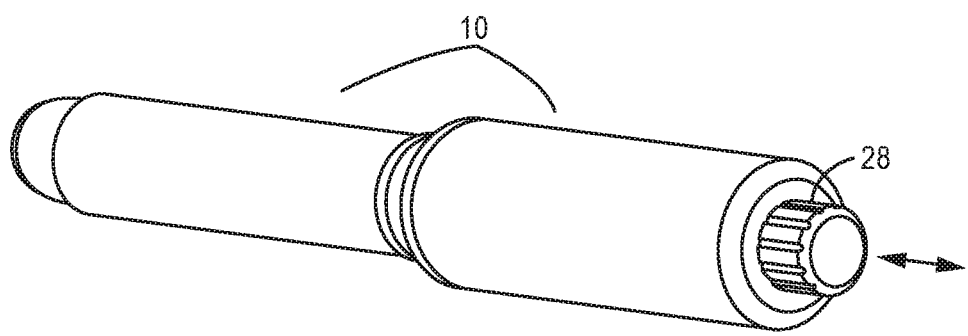
Figure 20:
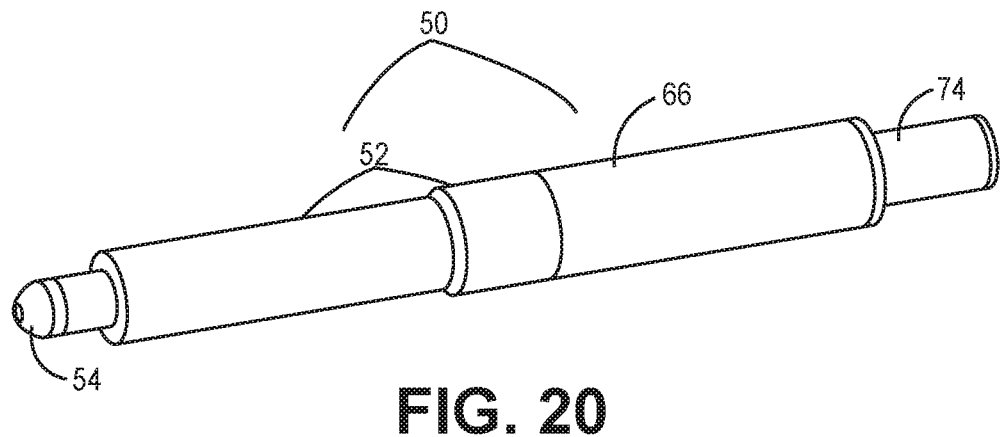
FIG. 20 is a perspective view of an embodiment of a metered dose applicator with a pushbutton.

The embodiment shown in FIGS. 19A and 19B can be realized with various arrangements of functional internal components. One such arrangement is metered dose topical applicator 50 shown in FIG. 20. Applicator 50 includes a barrel 52 and an applicator tip 54. Drive housing 66 is assembled and affixed to barrel 52. Pushbutton 74 is concentrically captured within drive housing 66, but is free to move axially, within limits.

Figure 21:
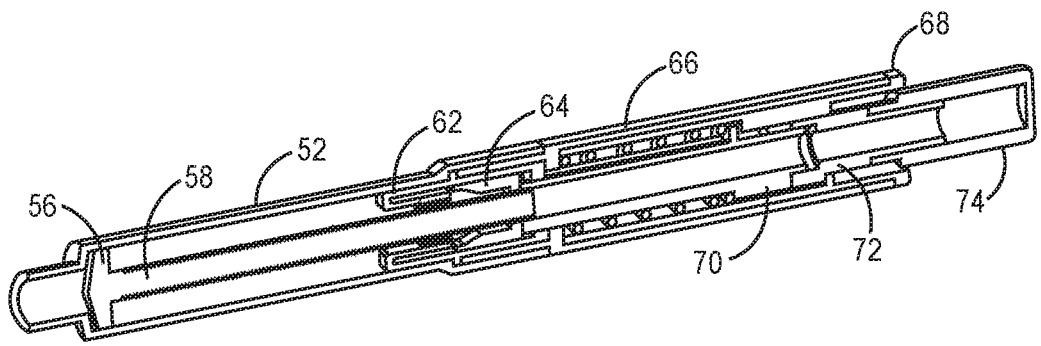
FIG. 21 is a cross-sectional view of the applicator of FIG. 20.

FIG. 21 shows the internal components of applicator 50, starting with an elevator 56 and a screw 58. In FIG. 21, applicator 50 is shown in the configuration as supplied to the preparing agency (e.g. compounding pharmacy) in a state ready to be filled with medicament-containing cream. Elevator 56 and screw 58 can be a single component or an assembly of two affixed components, the preferred configuration defined only by manufacturing considerations. Disposed within barrel 52 is nut 62, which will become engaged with screw 58 to drive elevator 56, as will be explained below. Disposed within drive housing 66 is locking wedge 64 that, when repositioned, will effect the engagement of nut 62 with screw 58. Also disposed within drive housing 66 is drive guide 68, which is concentrically and axially affixed to barrel 52. Disposed within drive guide 68 is drive actuator 70, which is free to rotate and to translate axially, within limits. Pusher 72 is also disposed within drive guide 68, and is free to translate axially, within limits. Pushbutton 74 is affixed to pusher 72, and is the external link accessible to the user to initiate the internal drive system functioning of applicator 50. Return spring 76 is disposed within drive housing 66, and serves to bias drive actuator 70 to a start position, which bias can be overcome by the operator pushing on pushbutton 74.

Figure 22:
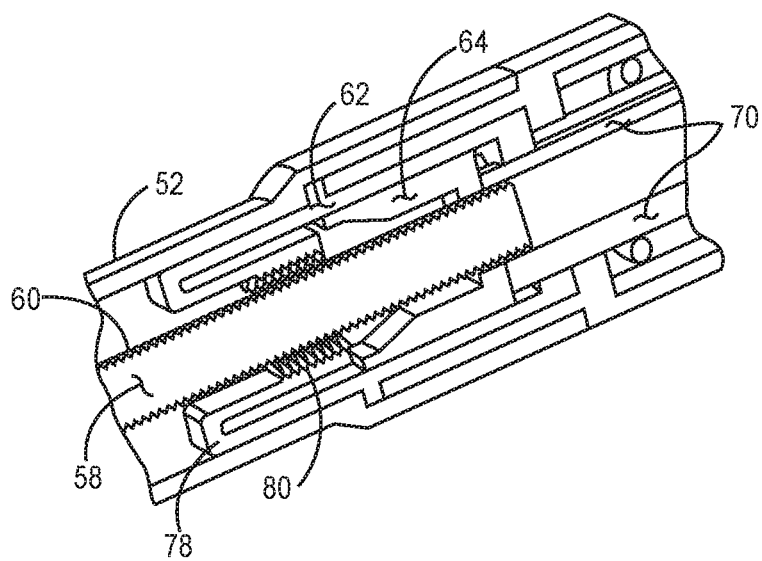
FIG. 22 is a detailed cross-sectional view of the applicator of FIGS. 20 and 21

Referring now to FIG. 22, nut 62 is shown within barrel 52 in the as-supplied configuration, i.e. ready to be filled. As with other embodiments of the present invention, nut 62 is not engaged with screw 58, which allows screw 58 (and elevator 56) to move axially during filling. Nut 62 includes two opposing flexible legs 78, on which threaded portions 80 are disposed. As shown threaded portions 80 are spaced away from screw 58. Screw 58 includes screw threads 60, but, because of the spacing, are not engaged with screw threads 60 in this configuration. Locking wedge 64, shown here not in contact with nut 62 and legs 78, serves to engage and lock the drive components, i.e. nut 62 with screw 58, together for dispensing doses, as described below. Drive actuator 70 contacts locking wedge 64 in this configuration, as shown, and will urge locking wedge 64 to the left when applicator 50 is operated via pushbutton 74.

Figure 23:
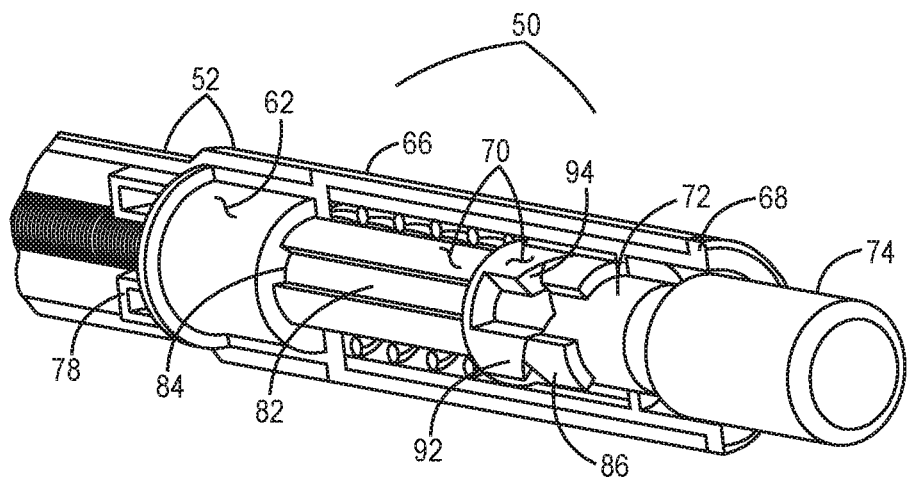
FIG. 23 is a perspective view of the applicator of FIGS. 20 to 22, with portions removed for clarity.

Referring now to FIG. 23, the assembled components of applicator 50 are shown in the same configuration as in the previous figure. Nut 62 is constrained axially, but is free to rotate about the axis, which rotation is accomplished with rotation of drive actuator 70. Drive actuator 70 includes guide slots 82 that cooperate with drive lugs 84 of nut 62, so that nut 62 rotates with drive actuator 70. Nonetheless, drive actuator 70 is allowed to translate along the axis, within limits. Pusher 72 contacts drive actuator 70 as shown, and axial translation of pusher 72 to the left will translate drive actuator 70 as well. As previously described, pushbutton 74 is affixed to pusher 72.

Figure 24:
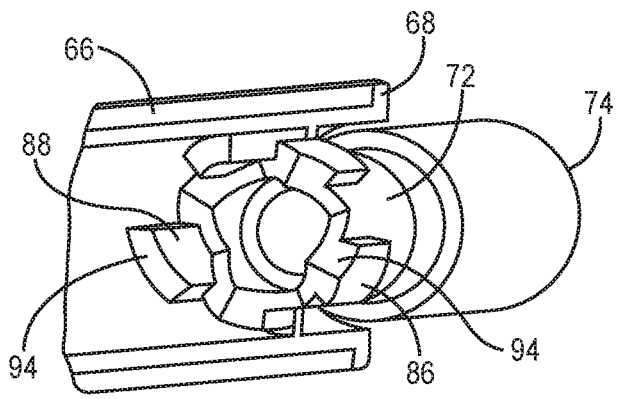
FIG. 24 is a detailed perspective view of the applicator of FIG. 23, with portions removed.
Figure 25:
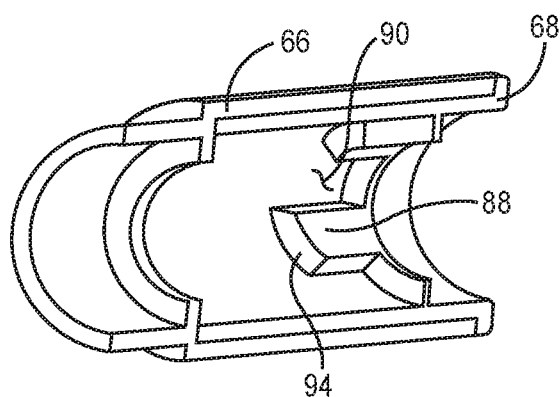
FIG. 25 is a detailed cross-sectional view of a components of the applicator of FIG. 24.

Referring now to FIG. 24 and FIG. 25, the physical relationship between pusher 72 and drive guide 68 is shown. Pusher 72 includes guide lugs 86. Drive guide 68 includes guide ribs 88, which form guide rib slots 90 (FIG. 25). Guide lugs 86 ride in guide rib slots 90 preventing pusher 72 from rotating during its allowed translation. Guide lugs 86, guide ribs 88, and pilot lugs 92 all include inclined planes 94, which function as cams translating linear to rotary motion as will be explained further below.

Another important feature of applicator 50 is best described now by referring back to FIG. 23. Just as guide lugs 86 of pusher 72 ride in guide rib slots 90 (FIG. 25) of drive housing 66, so, too, do pilot lugs 92 of drive actuator 70, preventing drive actuator 70 from rotating, but in this case for only a portion of the allowable translation. Once pilot lugs 92 are no longer constrained by guide rib slots 90, drive actuator 70 is free to rotate.

Having now defined the components of applicator 50, the function of the drive system will be explained. Generally, pushing pushbutton 74 translates pusher 72, which moves drive actuator 70 until it is no longer rotationally constrained. At that point, drive actuator 70 rotates by action of a spring force on inclined surfaces. This rotates nut 62. Once pusher 72 reaches its travel limit, pushbutton 74 is released, and drive actuator 70 rotates again by additional action of the spring force supplied by return spring 76 on a different pair of inclined surfaces. This again rotates nut 62. Rotation of nut 62 causes axial advancement of screw 58, and elevator 56, which do not rotate, to expel a dose.

This type of push-to-rotate mechanism is analogous, in part, to ordinary click-style ballpoint pens. In that case, the rotating member simply returns to either of two alternating positions, in or out, as the pushbutton is cycled. Adding female threads to the rotating member and a male-threaded screw, and eliminating the alternating return positions, are what make it into a dispensing mechanism rather than an alternating position mechanism. The aforementioned prior art device, the Topical CLICK pen available through RxCoop, uses a mechanism of this form.

Figure 26A:
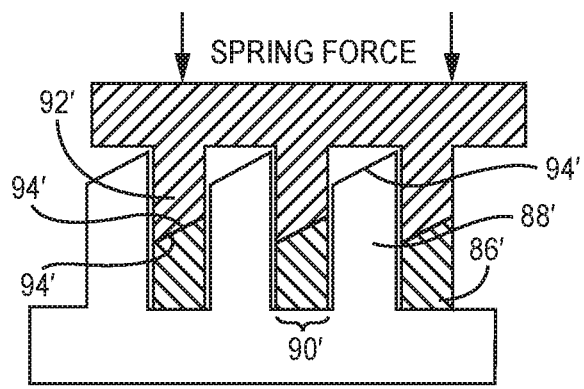
FIG. 26A to 26C are diagrammatic cross-sectional views of components of the applicator of FIGS. 20 to 25.
Figure 26B:
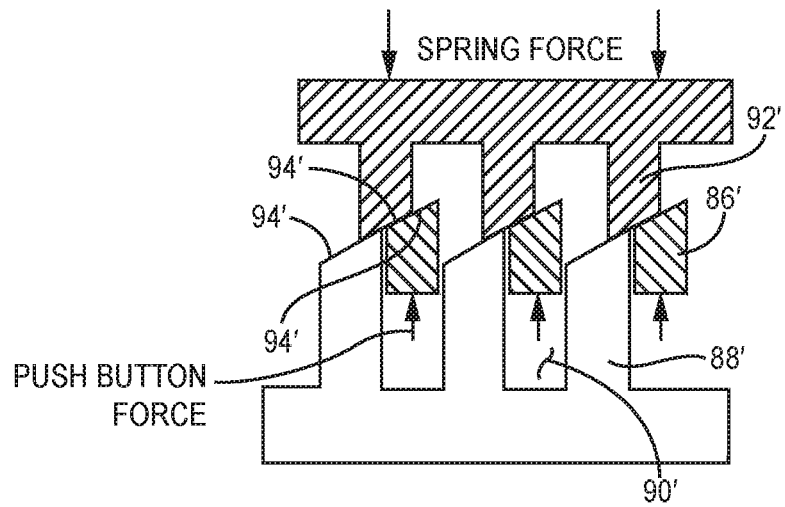
Figure 26C:
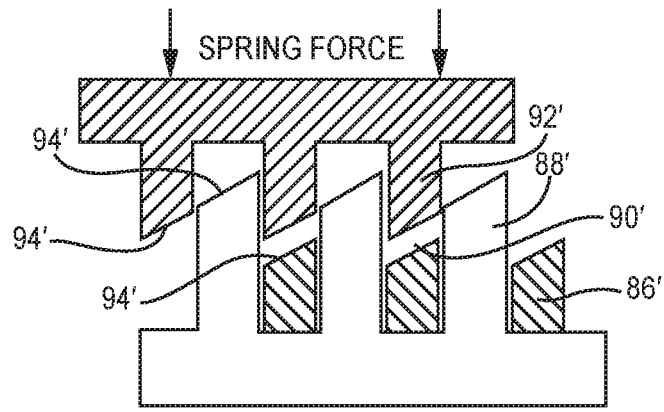

Referring to FIGS. 26A, 26B, and 26C shed additional light on the function of the drive mechanism of applicator 50. For easier visualization, these figures show, conceptually, the key components "unwrapped" from their round configuration. Entities shown are block diagram analogs of those as described above, but with their entity numbers denoted by a prime ('). In the start position shown in FIG. 26A, guide lug 86' and pilot lug 92' ride in guide rib slots 90'. As previously explained pushing pushbutton 74 translates pusher 72, and thus guide lug 86, and, in turn, pilot lug 92. Once pilot lug 92 moves beyond guide rib slot 90, it rotates as shown in FIG. 26B by action of the spring force on the mating inclined planes 94. When pushbutton 74 is released, all components return toward the start position, rotated, however, to the next indexed location, as shown in FIG. 26C.

Figure 27:
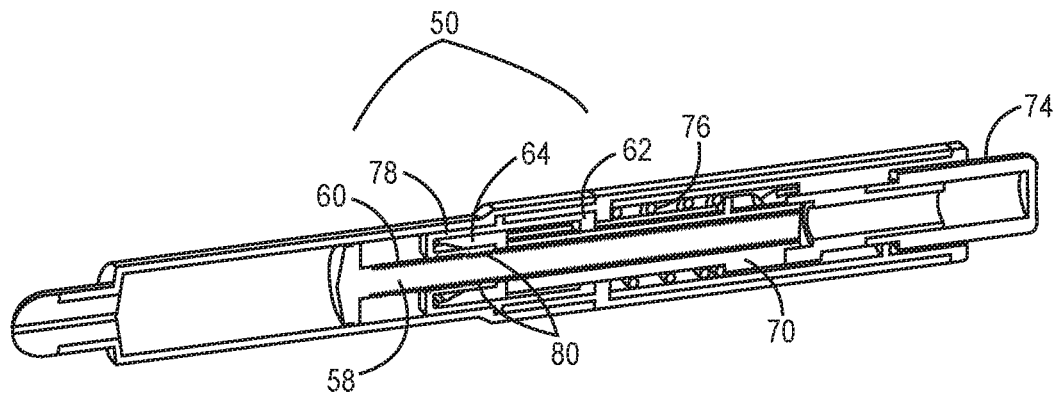
FIGS. 27 and 28 is cross-sectional views of the applicator of FIGS. 20 to 26C.
Figure 28:
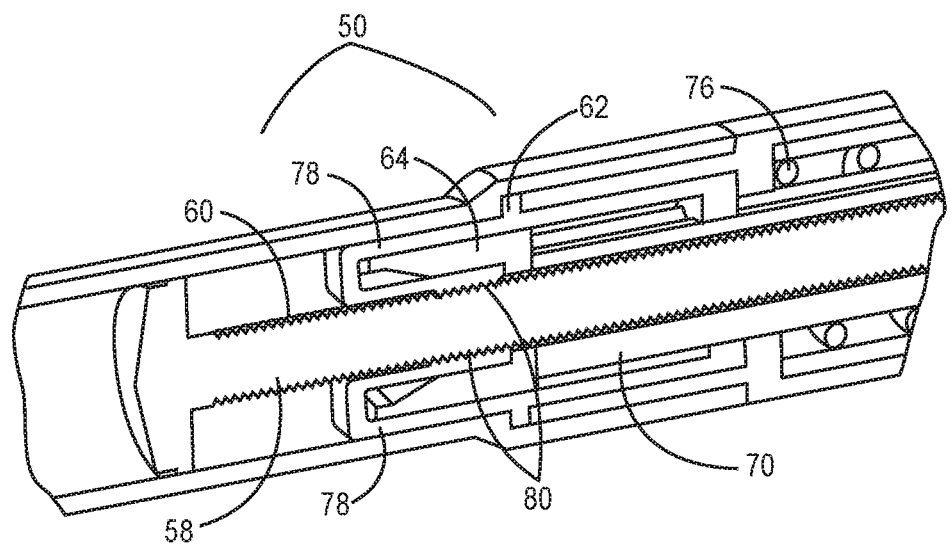

Referring again to FIG. 22, how the drive system of applicator 50 is changed from unengaged to engaged will be explained. Threaded portion 80 of nut 62 is not engaged with screw threads 60 of screw 58 in the as-supplied, ready-to-fill configuration. As previously explained, this allows applicator 50 to by filled with any desired volume of a flowable compound. Once filled, the operator pushes the pushbutton 74 to dispense metered doses as previously described. However, the first actuation of pushbutton 74 is what causes threaded portion 80 to engage with screw threads 60. This is shown in FIG. 27, and in detail in FIG. 28. Drive actuator 70, when moved via pushbutton 74, translates locking wedge 64 into a gap in nut 62 formed in legs 78, which flexes legs 78 in such a way to force engagement of threaded portion 80 with screw threads 60. Once in this position, locking wedge 64 remains there to keep the drive system engaged. FIG. 28 shows the now-engaged drive system in detail. Drive actuator 70 will be forced to return to its start position by return spring 76 once the operator releases pushbutton 74.

So to summarize, applicator 50 has a drive system that is initially unengaged, which allows any desired amount of cream to be filled. Once filled, the first push of the dosing pushbutton permanently engages the drive system. Thereafter, each push dispenses a metered dose.

Additional permutations of actuating the drive system after filling, and dispensing metered doses after that, are possible. For example, one variation of the embodiment shown in FIGS. 19A and 19B is to separate the drive actuation and dose activation functions into two different physical elements. Thus, this embodiment could include a side button as shown on FIG. 16A to actuate the drive, leaving pushbutton 28 with the sole function of activating metered doses.

Other embodiments in accordance to the present invention may be constructed that present a drive actuation feature in any location and with any motion, being restrained only by whatever action is most convenient for the user, and which internal arrangement of components yields best to manufacturability. For example, no strict adherence to the elevator-to-drive screw-to-drive nut-to-dosing knob configuration is required to practice the present invention. The drive nut could be attached to, or integral with, the elevator, with the drive screw then attached to the knob. In other words, component locations and relationships can be inverted or otherwise changed and still function in the manner herein disclosed.

The following patents are incorporated by reference for all purposes:
U.S. Pat. No. 949,163 to Stapley
U.S. Pat. No. 1,568,178 to Noble
U.S. Pat. No. 2,283,915 to Cole
U.S. Pat. No. 3,353,718 to McLay
U.S. Pat. No. 3,616,970 to Baumann et al.
U.S. Pat. No. 4,139,127 to Gentile
U.S. Pat. No. 4,810,249 to Haber, et al
U.S. Pat. No. 5,725,133 to Iaia
U.S. Pat. No. 5,851,079 to Horstman et al.
U.S. Pat. No. 6,129,471 to Lang
U.S. Pat. No. 6,551,611 to Elliesen et al.
U.S. Pat. No. 7,086,564 to Corrigan
U.S. Pat. No. 7,213,994 to Phipps et al.
U.S. Pat. No. 7,303,348 to Phipps et al.
U.S. Pat. No. 8,544,684 to Perez
U.S. Pat. No. 8,950,993 to Gagne et al.
U.S. Pat. No. 9,097,571 to Phipps et al.
U.S. Pat. App. 2014/0031323 to Perez
U.S. Pat. App. 2014/0221945 to Dos Santos et al.
U.S. Pat. App. 2016/0129228 to Perez
WO 2014/121259 to Dos Santos et al.
U.S. Pat. App. No. 2018/0178968 to Phipps, et al.
U.S. Pat. Pub. No. 2018/0207413 to Skakoon, et al.

The above disclosure is related to the detailed technical contents and inventive futures thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered by the spirit and technical theory of the subject invention.

While the disclosure is amenable to various modifications and alternative forms, specifics thereof have been shown by way of example in the drawings and described in detail. It is understood, however, that the intention is not to limit the application to the particular embodiments described. On the contrary, the intention is to cover all modifications, equivalents, and alternatives falling within the spirit and scope of the disclosure as defined by the appended claims.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

References to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art. "Portion" when used herein may refer to a portion of a discrete component, all of a component, or a portion of an assembly, that is, for example, two components of an assembly of 5 components may be a "portion", the terminology is not intended to be limiting.

For purposes of interpreting the claims, it is expressly intended that the provisions of 35 U.S.C. 112(f) are not to be invoked unless the specific terms "means for" or "step for" are recited in the respective claim.

The invention claimed is:
1. A topical applicator comprising:
a barrel with a first end and a second end;
an elevator slidably and sealably disposed within said barrel, the elevator attached to a threaded rod extending from the elevator toward the first end of said barrel, the barrel and elevator defining a reservoir;

an access port disposed on second end of said barrel through which flowable compounds may be added to or expelled from said reservoir;

a threaded nut with integral threads to engage threads of said threaded rod, said threaded nut including an integral knob, said nut and knob radially and axially constrained at first end of said barrel;

an actuating means disposed on or in relation to said barrel, wherein operating said actuating means toggles said threaded nut from disengaged to engaged with said threaded rod;

wherein said flowable compound can be added to said reservoir, causing said elevator to translate in a first axial direction of said barrel, when the actuating means has not engaged said threaded nut with said threaded rod, and, wherein rotating said knob in a first direction translates said elevator in a second axial direction of said barrel when actuating means has engaged said threaded nut with said threaded rod to expel said flowable compounds through said access port.

2. The topical applicator of claim 1, wherein rotating said knob in the first direction operates said actuating means.

3. The topical applicator of claim 1, further comprising an applicator tip attachable to said access port, said applicator tip including a topical applicator surface and a hole or holes to convey said flowable compound from said reservoir to said applicator surface.

4. The topical applicator of claim 3, wherein the access port comprises one of a male luer connector and a female luer connector, and wherein the applicator tip comprises the other of the male luer connector and the female luer connector.

5. The topical applicator of claim 3, wherein the applicator tip includes a substantially convex surface for applying said flowable compound topically.

6. The topical applicator of claim 1, wherein said threads on said threaded nut are formed on fingers that flex toward said threaded rod to engage with threads of said threaded rod.

7. The topical applicator of claim 6, wherein said actuating means includes a ring disposed on said barrel that is translated in a first direction to effect engagement of said threaded nut to said threaded rod.

8. The topical applicator of claim 1, wherein said actuating means includes a ring disposed on said barrel that is translated in a first direction to effect engagement of said threaded nut to said threaded rod.

9. The topical applicator of claim 1, wherein said actuating means includes a button disposed on said barrel that is pushed in a first direction to effect engagement of said threaded nut to said threaded rod.

10. The topical applicator of claim 1, wherein said actuating means includes a latching means in physical communication with said ring or button, said latching means maintaining engagement of said threaded nut to said threaded rod.

11. The topical applicator of claim 10 wherein said latching means is a ring slidably or rotatably disposed on said nut, said ring causing said fingers to flex, thereby engaging said threaded nut to said threaded rod.

12. The topical applicator of claim 11, wherein said ring cooperates with latching features on said fingers such that threaded nut remains engaged with threaded rod.

13. The topical applicator of claim 1, including a ratchet means to prevent rotation of said knob in a second direction.

14. A topical applicator having a fill mode and a dispense mode, the applicator comprising:
a medicament reservoir barrel with a first end and an opposite second end, the second end being a fill and dispense end;
an elevator slidably disposed within said barrel, the elevator connecting to a threaded rod extending away from the second end of said barrel, the barrel and elevator forming a reservoir, the elevator and connected threaded rod movable in a direction toward the first end when the applicator is in the fill mode for receiving a flowable medicament in the reservoir;
a rotatable knob with a circumferentially extending gripping surface, the rotatable knob at or rearward of the first barrel end, the rotatable knob coupled to a threaded nut portion configured for engaging threads of said threaded rod when the applicator is changed from the fill mode to the dispense mode, the applicator changeable from the fill mode to the dispense mode by a manual external actuation,
wherein the manual external actuation is by an axial movement of an actuator portion of the applicator.

15. A method of filling and using a topical applicator having a barrel with an elevator connection to a threaded member, a nut rotatable with respect to the barrel, the nut having a plurality of fingers with threaded portions movable from a disengaged position to an engaged position with the threaded rod, a manual handle for rotating the nut, the method comprising:
injecting a flowable compound into a reservoir defined by the barrel with the elevator in proximity to a fill and dispense end of the barrel with the plurality of fingers with threaded portions disengaged from the threaded rod whereby the elevator and threaded rod move away from the fill and dispense end of the barrel;
ceasing injecting the flowable compound when a desired amount is in the reservoir;
moving the plurality of fingers with threaded portions inwardly to the engagement position with the threaded rod.

16. The method of claim 15 further comprising moving the plurality of fingers with threaded portions inwardly by moving an actuator portion engaged with the plurality of fingers.

17. The method of claim 15 further comprising moving the plurality of fingers with threaded portions inwardly by axially moving an externally exposed actuator portion engaged or engageable with the plurality of fingers.

18. The method of claim 17 further comprising rotating the manual handle in a direction to translate the threaded rod and elevator toward the fill and dispense end of the barrel thereby ejecting the flowable compound out of the fill and dispense end.

* * * * *